United States Patent [19]

Rhodes et al.

[11] Patent Number: 4,752,372

[45] Date of Patent: Jun. 21, 1988

[54] MOVING WALL, CONTINUOUS FLOW ELECTRONPHORESIS APPARATUS

[75] Inventors: Percy H. Rhodes; Robert S. Snyder, both of Huntsville, Ala.

[73] Assignee: The United States of America as represented by the Administrator of the National Aeronautics and Space Administration, Washington, D.C.

[21] Appl. No.: 904,128

[22] Filed: Sep. 5, 1986

[51] Int. Cl.⁴ ...................... G01N 27/26; G01N 27/28
[52] U.S. Cl. ............................. 204/299 R; 204/180.1
[58] Field of Search ................ 204/301, 299 R, 180.1, 204/182.3

[56] References Cited

U.S. PATENT DOCUMENTS

| | | | |
|---|---|---|---|
| 3,755,132 | 8/1973 | Kolin et al. | 204/299 R |
| 3,847,773 | 11/1974 | Snyder | 204/299 R |
| 4,309,268 | 1/1982 | Richman | 204/301 |
| 4,310,408 | 1/1982 | Rose et al. | 204/301 |
| 4,358,358 | 11/1982 | Rhodes | 204/299 R |

FOREIGN PATENT DOCUMENTS 4044000  10/1984  Japan ................................ 204/299 R Primary Examiner—John F. Niebling
Assistant Examiner—John S. Starsiak, Jr.
Attorney, Agent, or Firm—William J. Sheehan; John R. Manning; Leon D. Wofford, Jr.

[57] ABSTRACT

A moving wall, continuous flow electrophoresis apparatus (10) having a frame (18) with an electrophoresis chamber (12) mounted between a pair of synchronously driven belt walls (14, 16). The frame (18), and thus the chamber (12), is supported between the belt walls (14, 16) and is angularly positionable with respect to the direction of belt travel. The belts are stored on supply reels (98, 156) at one end of the device and are taken up on driven reels (94, 132) at the other end, thus constantly exposing new belt material within the chamber.

12 Claims, 3 Drawing Sheets

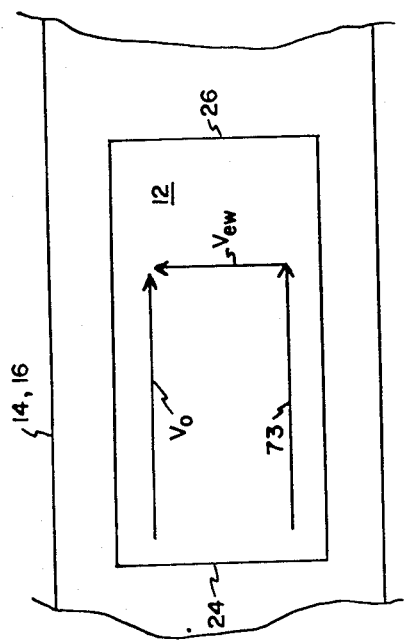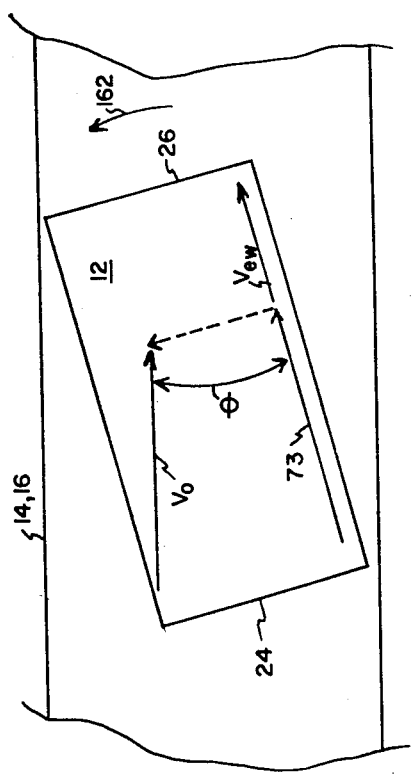

MOVING WALL, CONTINUOUS FLOW ELECTRONPHORESIS APPARATUS

ORIGIN OF THE INVENTION

The invention described herein was made by employees of the United States Government and may be manufactured and used by or for the Government for Government purposes without the payment of any royalties thereon or therefor.

TECHNICAL FIELD

This invention relates generally to the electrophoresis process wherein biological cells, colloidal particles, macromolecules and other organic particles having an electrical charge are separated in an electrical field in terms of their electrokinetic properties, and more particularly to an improved apparatus for implementing the process.

BACKGROUND OF THE INVENTION

Electrophoresis is not a new art, the first process of which was a moving boundary type described by Tiselius in 1937. It was used to study the movement and interactions of proteins. Since then, many methods have been devised for carrying out the process, and many papers have been published describing these processes.

To date, continuous flow electrophoresis devices have typically used a rectangular chamber having a very thin cross section which ranges from 0.05 to 0.15 cm. An electrolytic buffer solution is injected at one end of the chamber and drawn off at the opposite end, simultaneously filling and creating a flow through the chamber. Positive and negative electrodes are positioned opposite each other along the thin sides of the chamber, causing an electrical field to be impressed laterally across the width of the chamber. A sample stream containing a homogenous mixture of variously sized organic particles having different electrokinetic properties is injected at the same end of the chamber as the buffer so that it flows with the buffer through the chamber. As the sample stream flows through the chamber, the charged particles migrate toward oppositely charged electrodes a distance which is determined by the size of a particle, the viscosity of the buffer, and the strength of the charge on a particle. This causes species of particles to form bands across the width of the chamber, which are collected by a collection array along with a quantity of buffer commensurate with the sum of the injected buffer and sample. Thus, by continuously injecting a buffer and sample stream of particles, a continuous collection of fractionated species particles (and buffer) is accomplished.

Problems arise, however, because flow dynamics in the aforementioned chamber cause distortions of the separated species particles. One of these distortions, known as Poiseuille flow, is induced from frictional effects of the walls of the chamber on adjacent fluid flow. This causes particles flowing along the chamber walls to move slower and reside in the chamber for a longer period of time than particles flowing along the mid plane of the chamber, allowing the slower particles to migrate laterally a further distance than mid plane particles. Thus, when viewed from the collection end of the chamber, a crescent-shaped band is formed, with the nose of the crescent generally in the mid plane of the chamber and the tails of the crescent nearer their respective walls.

A second flow distortion, known as electroosmosis, is a bidirectional lateral flow across the width of the chamber. This is caused by a phenomenon known as the zeta potential, which generally is due to a weak negative charge at the chamber walls when a hydrated ionic solution is present. The negatively charged walls in turn attract positive ions from the solution, which form a layer of positive ions on the surfaces of each of the chamber walls. Being only weakly attracted to the walls, the positive ions are pulled along the chamber walls under the influence of the negative electrode, which generates a fluid flow along the walls in a direction toward the negative electrode. Because the sides of the chamber are closed, a corresponding counterflow in the mid plane of the chamber, in an opposite direction, is generated which causes the injected sample stream to form a parabolic crescent, with the nose of the crescent (generally in the mid plane of the chamber) to be pointed toward the positive electrode, while the tails of the crescent (along the walls) are drawn toward the negative electrode. A more thorough discussion of these problems may be found in Strickler, A. and Sacks, T. *Preparative Biochemistry*, 3, p. 269–277 (1973).

These two aforementioned problems, Poiseuille flow and electroosmosis, combine in a conventional continuous flow electrophoresis device to form crescent-shaped distortions of the separated species particles which makes the collection of the separated particles difficult, if not impossible. Several attempts to compensate or eliminate these effects have been tried but have proved to be ineffective or impractical. While these methods can bring one species band of particles into focus, to date, none have been demonstrated which are able to bring all species bands into focus simultaneously. One such method to eliminate flow disturbances was proposed by A. Kolin and B. L. Ellerbroek in a paper entitled "Theory of Simultaneous Multiple Streak Collimation in Continuous-Flow Electrophoresis by Superposition of Electro-Osmosis and Thermal Convection," *Separation and Purification Methods*, 8, 1–19 (1979). This method utilizes a cross flow to neutralize electroosmosis and uses thermal convection to dampen the Poiseuille effect so that the center plane region of the chamber will be relatively distortion-free. The problem with this scheme, however, is that exact calibration of the counter flow to compensate for electroosmosis throughout the length of the chamber is virtually impossible to achieve.

Another proposed method for compensating for flow disturbances in continuous flow electrophoresis devices is set forth in Strickler, A. and Sacks, T., "Focusing in Continuous Flow Electrophoresis System by Electrical Control of Effective Cell Wall Zeta Potential," *Annals of New York Academy of Science*, 209 (1973). This scheme consisted of coating longitudinal sections of the chamber with various coatings having different zeta potentials and having separate electrodes for each differently coated section. The electrical field in each section may be independently varied as a sample passes through the chamber, thus compensating for flow distortions in fractionated species acquired in a prior coated section. Although this method is workable, it is necessary to control the process by visual observation, which is operator intensive and therefore somewhat impractical.

Yet another electrophoresis device is disclosed in U.S. Pat. No. 4,358,358 which uses a pair of endless, wide Mylar TM belts which form the broad walls of an electrophoresis chamber which is supported in a tank of buffer solution. The surfaces of these belts which face the chamber are coated with Methylcellulose which has a zeta potential near zero. The belts are synchronized to simultaneously move across the electrophoresis chamber at the same rate as the buffer flow, which entrains the buffer to flow through the chamber as a rigid medium, eliminating problems associated with Poiseuille flow. In theory, this is a workable system because there would be no flow distortions to compensate for and no electroosmosis flow because there would be no charge on the moving walls because of the Methylcellulose coating. It has been discovered, however, that Methylcellulose and other wall coatings are not particularly stable, resulting in difficulty in maintaining a zero zeta potential coating. Additionally, any contamination of the coating by the sample increases the zeta potential of the coating. Further, contact between the wall coating and the necessary seals and reels tends to have an abrasive effect on the wall coatings, causing an increase in the zeta potential. Still further, the chamber and belt drives were immersed in an enclosure containing an electrolytic solution, which presented operational inconveniences. As a result of these problems, the device disclosed in U.S. Pat. No. 4,358,358 is difficult to operate reliably.

Accordingly, it is an object of this invention to provide a moving wall, continuous flow electrophoresis device which will, by entraining the buffer to flow as a rigid body through the electrophoresis chamber, eliminate flow distortions from the Poiseuille effect.

Another object of this invention is to provide a moving wall electrophoresis device which will exactly compensate for electroosmosis flow by a simple mechanical adjustment, bringing all fractionated species particles into focus simultaneously.

Yet another object of this invention is to provide a moving wall, continuous flow electrophoresis device which is not operator intensive.

SUMMARY OF THE INVENTION

In accordance with this invention, a moving wall, continuous flow electrophoresis device is constructed having a pair of spaced moving belt walls. A frame incorporating an electrophoresis chamber is sealably positioned between the belts and is rotatably supported whereby the frame, and thus the chamber, is angularly positionable with respect to the direction of travel of the belts. Each belt is stored on separate supply reels at one end of the device and is taken up by separate, driven take-up reels at an opposite end, which continuously exposes new belt material within the chamber.

BRIEF DESCRIPTION OF THE DRAWINGS

FIG. 5a is a diagrammatic view of fluid flows in the present invention before the electrophoresis chamber is angularly displaced.

FIG. 5b is a diagrammatic view of how fluid flows shown in FIG. 5a are modified to cancel electrophoresis by angularly displacing the electrophoresis chamber.

DETAILED DESCRIPTION OF THE DRAWINGS

Figure 1:
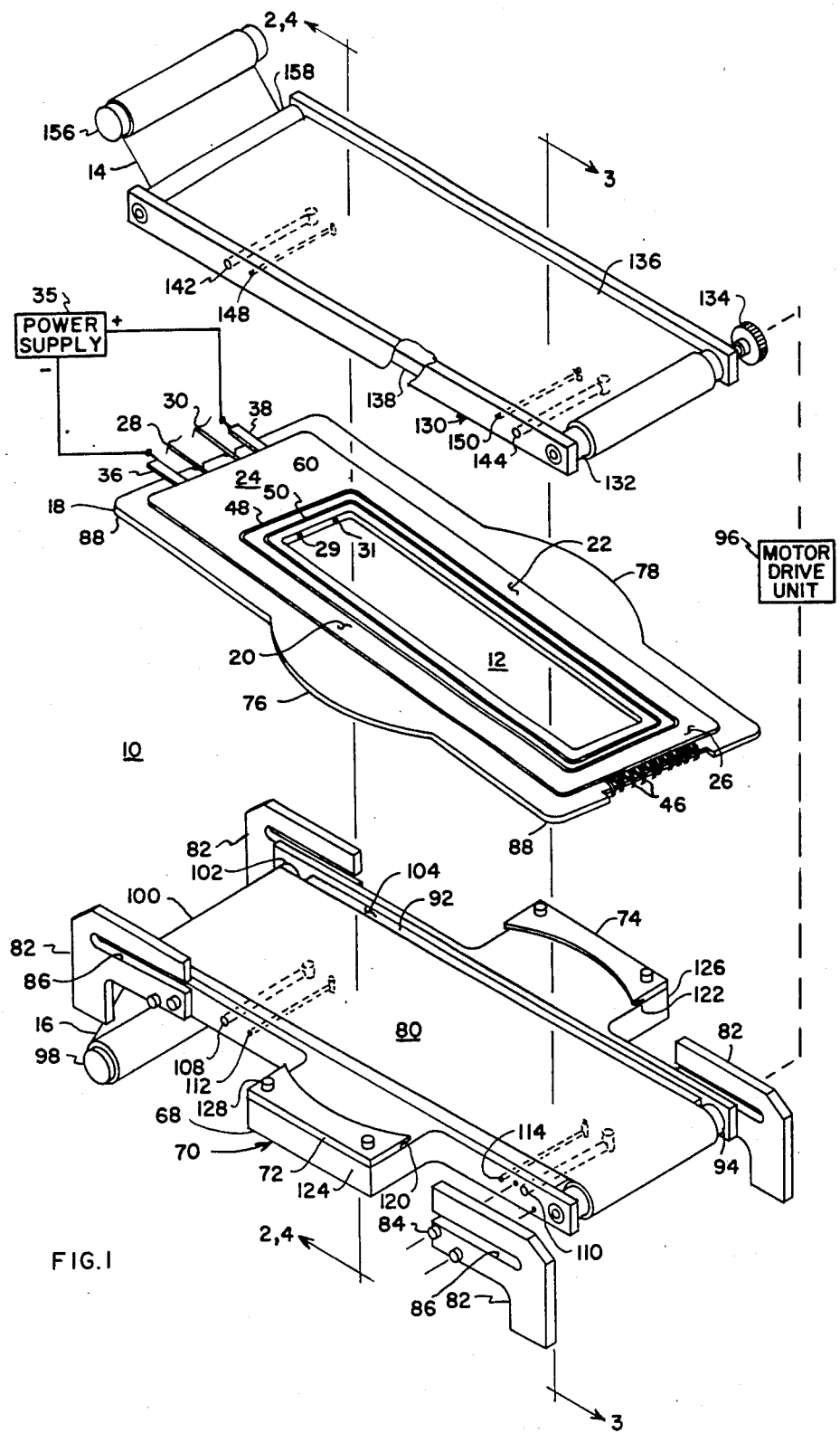
FIG. 1 is an exploded view in perspective of a preferred embodiment of this invention, with parts partially broken away and details of interior construction shown in dotted lines.
Figure 2:
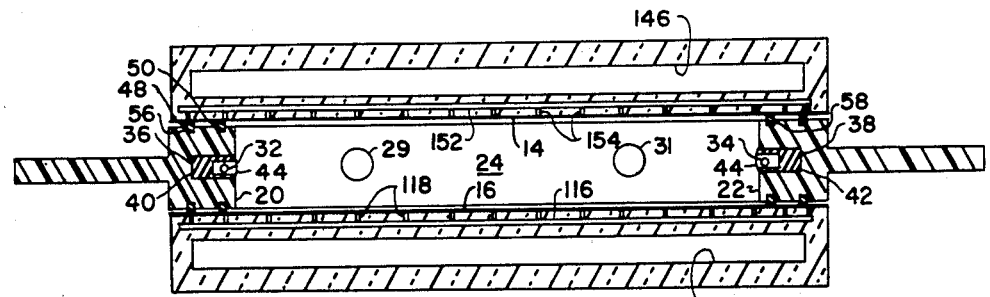
FIG. 2 is a diagrammatic sectional view taken along line 2—2 of FIG. 1, with construction details enlarged for clarity.
Figure 3:
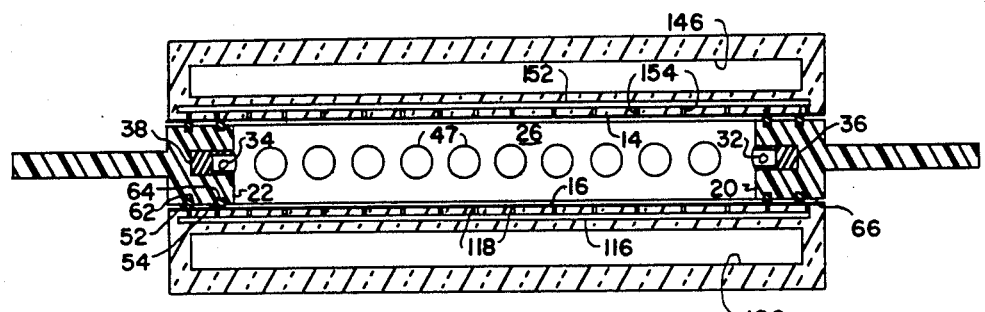
FIG. 3 is a diagrammatic sectional view taken along line 3—3 of FIG. 1, with construction details enlarged for clarity.
Figure 4:
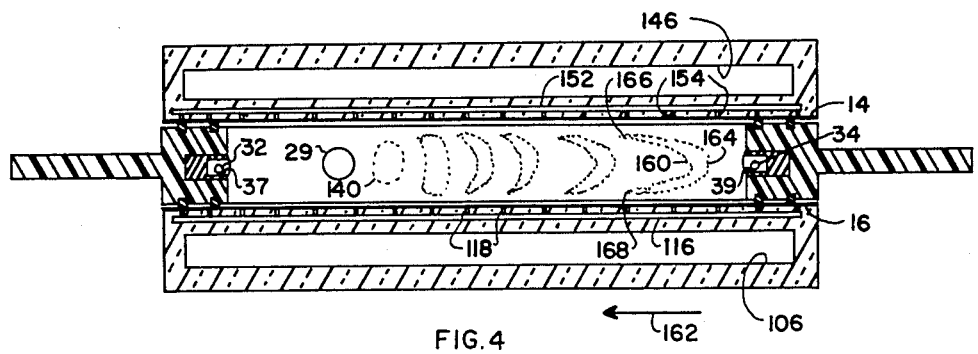
FIG. 4 is a diagrammatic sectional view taken along line 4—4 of FIG. 1, with construction details enlarged for clarity and dotted lines illustrating details of operation.

Referring initially to FIG. 1, a continuous flow, moving wall, electrophoresis apparatus 10 is illlustrated in an exploded view wherein an electrophoresis chamber 12 is formed by an upper belt 14, a lower belt 16, and a rectangular frame 18 positioned between the belts. Referring additionally to FIGS. 2, 3, and 4, sides of chamber 12 are formed by side wall regions 20 and 22 and end wall regions 24 and 26. Tubes 28 and 30 extend through end wall region 24, tube 30 supplying a buffered electrolytic solution via opening 31 to fill chamber 12, tube 28 providing an entrance passageway via opening 29 for a homogenous fluid consisting of a variety of organic particles suspended in a like buffered solution to that filling chamber 12.

Side wall regions 20 and 22 are constructed having cavities 40 and 42 which open into and extend the length of chamber 12. A pair of electrode supports 36 and 38 consisting of elongated strips of insulative material having recesses 37 and 39 (FIG. 4), respectively, are positioned within cavities 40 and 42. A pair of electrodes, negative electrode 32 and positive electrode 34 (FIG. 2), is supported within and extends the length of recesses 37 and 39 and is connected as shown to a conventional electrophoretic power supply 35. Recesses 37 and 39 are covered by a cellulose acetate membrane 44 and thus effect an enclosure of the recesses with respect to chamber 12. A conductive fluid, such as the same buffer solution referred to above, is introduced into recesses 37 and 39 by passageways not shown. The membranes 44 are also conductive, and thus there is provided a continuous conductive path from the electrodes, through the buffered solution, through membrane 44, and into chamber 12, also having a buffered solution. By this approach, there is electrical current flow but no fluid transfer between recesses 37 and 39 and chamber 12. This prevents disruptive effects which ordinarily might be associated with the transfer of electrical current from an electrode to a fluid, namely, formation of bubbles, heating, etc., which would then be confined within recesses 37 and 39. When isoelectric focusing is to be performed, dissimilar electrolytic fluids would be introduced into electrode recesses 37 and 39 and electrophoresis chamber 12. For example, this would be the process employed where ampholine is used as a buffer solution in chamber 12 as it would establish a pH gradient across the width of chamber 12. In such case, a low pH solution would be injected into anode electrode recess 39 and a higher pH solution in opposite cathode electrode recess 37. This would enable a match of the pH of amploline along sides 20 and 22 of chamber 12. Further, instead of a sample stream being injected through tube 28, the sample would be mixed with the amploline and injected through one of the tubes, 28 or 30.

A conventional sample collection array of tubes 46 extends from end region 26 of frame 18 and serves to continuously collect, via openings 47 (FIG. 3), as an output, fractionated species of particles in a quantity of buffer forming the sample stream flowing through chamber 12.

The sealing of chamber 12 is effected by upper seals 48 and 50 which seal between the upper side of frame 18 and upper belt 14 and like lower seals 52 and 54 which seal between the lower side of frame 18 and lower belt 16. Upper seals 48 and 50 are located in recesses 56 and 58, respectively, of top surface 60 of frame 18, and lower seals 52 and 54 are located in recesses 62 and 64 (FIG. 3), respectively, of bottom surface 66 of frame 18. A sliding seal is thus effected which prevents leakage of buffer solution from between belts 14 and 16 and top and bottom surfaces 60 and 66 and may be constructed of conventional resilient seal material or may consist of an inflatable seal.

Frame 18 is supported by a support structure 68 which is integral with lower belt assembly 70. it includes a pair of receptacles 72 and 74 in which lobes 76 and 78 of frame 18 are rotatably mounted, allowing frame 18 to be rotated about an axis 17 normal to an axis 19 extending longitudinally from belt walls 14 and 16 and thus vary alignment of flow with respect to the direction of movement of belts 14 and 16. This rotation may be accomplished manually or by chamber rotator 79 coupled to end 27 of frame 18. Rotator 79, when used, is responsive to computerized optical scanning equipment (not shown). Legs 82 attach to lower support 68 as by bolts 84 to support the apparatus on a stable surface and include slots 86 which provide clearance for corners 88 of frame 18 when frame 18 is rotated, as will be described.

Lower belt assembly 70 includes a generally flat plate 92 of thermally conductive material, such as aluminum, which supports belt 16 as it is pulled across plate 92 by drive reel 94. Reel 94 is rotated by a drive member (not shown) which in turn is operated by a conventional motor drive unit 96. Belt 16 is formed of a generally transparent material, such as Mylar ™, which is uncoated and has a constant zero potential, the belt being stored on a storage reel 98 mounted at end 100 of plate 92, by means not shown. An idler reel 102 is also mounted to end 100 and serves to distribute stresses on belt 16 and generally aligns belt 16 with upper surface 104 of plate 92. Plate 92 includes a coolant cavity and manifold 106 (FIGS. 2, 3, and 4), and coolant flow into and out of it is provided by coolant inlet 108 and outlet 110 (FIG. 1). Coolant is circulated through the manifold to maintain a relatively constant temperature in electrophoresis chamber 12. Vacuum ports 112 and 114 built into plate 92 are similarly connected by a spaced arrangement of channels 116 (only one shown in FIGS. 2, 3, and 4) which in turn are connected to a series of small spaced openings 118 in upper surface 104 of plate 92. A vacuum on the order of from 1 to 10 PSIG vacuum is applied to ports 112 and 114, which is communicated to openings 118 via channels 116 and draws belt 16 firmly against surface 104, providing resistance against drive reel 94 and assisting in keeping belt 16 taut over the length and width of plate 92. As stated earlier, a pair of removable receptacles 72 and 74 having semi-circular slots 120 and 122 adapted for rotatably receiving lobes 76 and 78 of frame 18 is attached to mounts 124 and 126 by bolts 128.

Upper belt support assembly 130 is similarly constructed of a transparent material to facilitate observation and has a drive reel 132 having a gear 134 which is operated by motor drive unit 96. Drive reel 132 on upper plate 136 and drive reel 94 on lower plate 92 are synchronously driven by motor drive unit 96, thus pulling upper belt 14 and lower belt 16 at precisely the same speed across their respective surfaces 104 and 138. This speed is calibrated to match the velocity of the flow of the injected buffer solution filling and flowing through chamber 12 and the injected sample stream 140 (FIG. 4, dotted line position), eliminating any flow distortions of the sample stream and the fractionated species particles due to the Poiseuille effect. Cooling inlet 142 and outlet 144 of plate 136 allow coolant to be circulated in manifold 146 (FIGS. 2, 3, and 4) and assist in keeping the buffer fluid at a constant temperature. Vacuum ports 148 and 150 are connected to vacuum channels 152 and communicate with small spaced openings 154 in lower surface 138 of upper plate 136 and perform the same function as their counterparts in lower plate 92. Additionally, a second supply reel 156 stores upper belt 14, and an idler reel 158 aligns belt 14 with lower surface 138 of upper belt support assembly 130.

In operation, and referring additionally to FIGS. 4, 5a and 5b, a buffer solution is injected into chamber 12 via opening 31 (not shown in FIG. 4 for clarity) until chamber 12 is filled. Power is applied to motor drive unit 96, which in turns pulls belts 14 and 16 across chamber 12 as described, which continuously exposes new belt material having a constant zeta potential within chamber 12. As buffer is continuously flowing through chamber 12 at an identical rate $V_o$ to that of the speed of belts 14 and 16, the solution in chamber 12 is entrained to move as a rigid body from end 24 to end 26 of chamber 12. Positive and negative potentials are applied to electrodes 34 and 32, respectively, from power supply 35. Sample stream 140 containing particles to be separated is injected in chamber 12 via opening 29 and, as shown in FIG. 4, a single species being fractionated is represented by dotted line positions as the species is moved the length of chamber 12 by buffer flow 73 and moved across the width of chamber 12 by electroosmotic flow $V_{ew}$. Due to electroosmotic flow $V_{ew}$ and the species forms a crescent of 160 of which only a small portion can be collected by collection array 46. It is to be understood that although only a single species is shown, several species may be fractionated in the same chamber. Sample stream 140 is observed through upper plate 136 as it travels the length of chamber 12; and if the various species broaden as they are fractionated (indicating crescent formation), then end 26 of frame 18 is rotated manually or by automated chamber rotator 79 in the direction of arrow 162 a slight amount (less than 5 degrees). As is known, electroosmosis is a buffer cross-flow circulation oriented generally perpendicular to sample stream 140 and which is driven by an electrical charge that accrues on the walls of the chamber and the charges on electrodes 32 and 34. The electroosmotic buffer cross-flow $V_{ew}$ (FIG. 5a) has a particular velocity, as does buffer flow 73 through chamber 12. Thus, by angularly displacing chamber 12 (FIG. 5b) so that electroosmotic cross-flow $V_{ew}$ (dotted lines) is angularly opposed by belt travel $V_o$, a resultant cross-flow in the direction of belt travel $V_o$ of belt walls 14 and 16 can be made to occur which will oppose and cancel electroosmotic cross-flow circulation $V_{ew}$. This can be expressed by a mathematical equation wherein $\theta$ is the angular difference between buffer flow 73 through chamber 12 and the direction of travel $V_o$ of belt walls 14 and 16:

$$\theta = \tan^{-1}(V_{ew}/V_o)$$

where $V_{ew}$ is the electroosmotic velocity of buffer at the walls and is expressed in cm/sec., and $V_o$ is the buffer flow-through velocity, also expressed in cm/sec. By using this formula in conjunction with existing computers and optical scanning equipment, it is possible to construct an automated electrophoresis apparatus which will require little operator interface, maintain an optimum belt speed to eliminate crescent formation due to flow dynamics (Poiseuille flow), and compensate for electroosmosis in a manner which allows simultaneous focusing of all species particles.

We claim:

1. A moving wall, continuous flow, electrophoresis apparatus for separating a plurality of species of particles into discrete species bands, said separation being effected in a fluid in accordance with electrokinetic properties of said particles, said apparatus comprising:

a pair of longitudinally extending movable walls positioned in longitudinal alignment with facing surfaces, said surfaces being uncoated and having a constant zeta potential;

a generally flat rotatable frame disposed between, and having facing regions in sealing engagement with, said surfaces of said walls, said frame including first and second side regions and first and second end regions, said first and second side and said first and second end regions being configured to provide a central opening, and with said pair of movable walls, from said opening forming a central electrophoresis chamber;

at least one fluid insertion means extending through said first end region into said chamber for continuously filling and effecting a flow through said chamber with an electrically conductive fluid and for inserting said plurality of species of particles into said fluid;

first and second electrode means in electrical contact with said fluid, and biasing means coupled to said electrodes, said first electrode means positioned along said first side wall of said frame, and said second electrode means positioned along said second side wall of said frame, for establishing an electrical field in said fluid;

a plurality of fluid exit passageways through said second end region of said frame;

drive means for continuously moving said pair of walls longitudinally in a direction away from said fluid insertion means, whereby said fluid is continuously moved by said pair of walls from said insertion means to said exit passageways;

support means for rotatably supporting said frame for rotation about a first axis extending normal to a longitudinal axis of said moving walls; and rotation means for rotating said frame;

whereby electroosmosis is nullified and said species bands are focused as they are moved through said chamber and collected by said plurality of fluid exit passageways.

2. An apparatus as set forth in claim 1 wherein:

said pair of walls comprises flexible belt walls; and said drive means includes reels at each end of said belt walls, reels at one end providing a supply of fresh belt walls, and reels at an opposite end providing a take-up of spent belt walls, whereby new belt wall material is continuously being exposed within said chamber.

3. An apparatus as set forth in claim 2 wherein said frame includes first and second lobes, and said support means includes matching receptacles for accommodating said curved lobes, whereby said frame, and thereby said chamber, is variable in alignment with said moving walls.

4. An apparatus as set forth in claim 3 wherein at least one piable seal is positioned on each side of said frame around said opening in said frame, whereby said seals provide a sealing engagement between said frame and said moving walls.

5. An apparatus as set forth in claim 4 wherein said first and second electrode means each comprises:

an elongated electrode disposed in a generally U-shaped channel of insulating material, said channels extending along said first and second side walls of said frame, and a conductive membrane closing said channels from said chamber and a conductive fluid filling said channels; and biasing means for applying a positive bias to one of said electrodes and a negative bias to an opposite electrode, said biasing means being with respect to ground;

whereby an electrical field is established between said electrodes in said chamber.

6. An apparatus as set forth in claim 1 wherein electroosmosis is cancelled responsive to rotational movement of said frame through an angle defined by $\theta$ and expressed:

$$\theta = \mathrm{TAN}^{-1}(V_{ew}/Y_o)$$

whereby $V_{ew}$ is electroosmotic velocity of fluid at said moving wall and is expressed in cm/sec, and $V_o$ is fluid flow-through velocity and is expressed in cm/sec.

7. In an improved continuous flow electrophoresis apparatus of the type having an electrophoresis chamber having a pair of broad, facing, moving walls, and first fluid insertion means for filling and continuously enabling a flow through said chamber with an electrically conductive fluid, and second fluid insertion means for inserting a homogenous suspension of a plurality of species of particles into said conductive fluid flowing through said chamber, and first and second electrode means for establishing an electrical field in said chamber, whereby said electrical field effects a lateral, differential migration of said particles separating said particles into discrete species bands, and collection means for collecting said discrete species bands wherein the improvement comprises:

a generally flat frame having first and second end walls and first and second side walls, said first and second end walls and said first and second side walls, with said pair of moving walls, forming an electrophoresis chamber therebetween, said first and second fluid insertion means being disposed in said first end wall, and said collection means being disposed in said second end wall, and said first and second electrode means being disposed along said first and second side walls, respectively, said frame being rotatably supported between said pair of moving walls, and means for rotating said frame, whereby each said discrete species band is simultaneously focused for collection thereof.

8. An improved electrophoresis apparatus as set forth in claim 7 wherein said frame is angularly displaced a predetermined amount, said amount being defined by $\theta$ and expressed:

$$\theta = \text{TAN}^{-1}(V_{ew}/V_o)$$

where $V_{ew}$ is the electroosmotic velocity of said fluid flow at the walls and is expressed in cm/sec, and $V_o$ is said fluid flow-through velocity and is also expressed in cm/sec.

9. In a method of continuous flow electrophoresis, wherein a plurality of species of particles is injected into an electrically conductive fluid filling and flowing through a moving wall electrophoresis chamber, for separating said particles into at least one species band, the improvement of angularly varying the flow of said fluid with respect to a direction of travel of said moving walls, for focusing said species band prior to collection thereof.

10. A method of electrophoresis as set forth in claim 9 wherein said chamber is defined by a generally flat frame having first and second oppositely positioned end walls and first and second oppositely positioned side walls, said frame being positioned between first and second broad facing walls disposed for movement in a direction toward an exit point of said species band of particles and comprising the step of angularly displacing said frame about an axis normal to a longitudinal axis of said first and second broad facing moving walls so that said separated species band is focused for passage out of said chamber.

11. A method of electrophoresis as set forth in claim 10 comprising the step of defining said angular displacement of said frame as 0 and expressing $\theta$ as $$\theta = \text{TAN}^{-1}(V_{ew}/V_o)$$

where $V_{ew}$ is the electroosmotic velocity of fluid flow at the moving walls and is expressed in centimeters/sec, and $V_o$ is the fluid flow-through velocity and is also expressed in cm/sec.

12. A method of electrophresis as set forth in claim 11 comprising the step of collecting said separated and focused species bands as they exit said chamber.

* * * * *